(12) United States Patent
Jeanne et al.

(10) Patent No.: US 9,579,079 B2
(45) Date of Patent: Feb. 28, 2017

(54) DEVICE AND METHOD FOR DETERMINING ACTUAL TISSUE LAYER BOUNDARIES OF A BODY

(75) Inventors: Vincent Jeanne, Eindhoven (NL); Sebastian Maeueler, Leopoldshohe (DE); Caifeng Shan, Eindhoven (NL)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 611 days.

(21) Appl. No.: 13/997,482

(22) PCT Filed: Dec. 27, 2011

(86) PCT No.: PCT/IB2011/055959
§ 371 (c)(1),
(2), (4) Date: Jun. 24, 2013

(87) PCT Pub. No.: WO2012/093317
PCT Pub. Date: Jul. 12, 2012

(65) Prior Publication Data
US 2013/0289409 A1 Oct. 31, 2013

(30) Foreign Application Priority Data
Jan. 5, 2011 (EP) .................... 11150150

(51) Int. Cl.
*A61B 8/00* (2006.01)
*A61B 8/08* (2006.01)
(Continued)

(52) U.S. Cl.
CPC .......... *A61B 8/0858* (2013.01); *A61B 5/4872* (2013.01); *G06T 7/0012* (2013.01);
(Continued)

(58) Field of Classification Search
CPC .... G06T 7/0012; G06T 7/0085; G06K 9/4647
See application file for complete search history.

(56) References Cited

U.S. PATENT DOCUMENTS 5,060,652 A * 10/1991 Umemura et al. ............ 600/447
5,520,183 A * 5/1996 Lake et al. .................... 600/453
(Continued)

FOREIGN PATENT DOCUMENTS

CN 101198981 A 6/2008
CN 101821608 A 9/2010
(Continued)

OTHER PUBLICATIONS

Fanelli et al: "Ultrasound as an Approach to Assessing Body Composition": The American Journal of Clinical Nutrition, May 1984, pp. 703-709.
(Continued)

*Primary Examiner* — James Kish

(57) ABSTRACT

The present invention relates to a device (8) for determining tissue layer boundaries of a body (14), comprising a probe (10) for acquiring (S12) two or more ultrasound images (36) at adjacent positions of a surface (12) of the body (14), a converter (44) for converting (S14) said ultrasound images (36) separately to depth signals (46), wherein a depth signal (46) is obtained by summing intensities of one of said ultrasound images (36) along a line (66) of substantially constant depth in the body (14), a detector (48) for detecting (S16) a set of candidate tissue layer boundaries (50) for an ultrasound image (36) by thresholding the depth signal (46) obtained for said ultrasound image (36), a selection means (52) for selecting (S18) from a set of candidate tissue layer boundaries (50) a nearest candidate tissue layer boundary (54) that is nearest to the surface (12) of the body (14), and a processing means (56) for determining (S20) an actual
(Continued)

tissue layer boundary (58) from the nearest candidate tissue layer boundaries (54) obtained for various ultrasound images (36).

14 Claims, 7 Drawing Sheets

(51) Int. Cl.
  *A61B 5/00* (2006.01)
  *G06T 7/00* (2006.01)
(52) U.S. Cl.
  CPC ........... *A61B 5/7239* (2013.01); *A61B 8/4254* (2013.01); *A61B 8/46* (2013.01)

(56) References Cited

U.S. PATENT DOCUMENTS

| | | | |
|---|---|---|---|
| 5,734,739 A * | 3/1998 | Sheehan et al. | 382/128 |
| 5,941,825 A | 8/1999 | Lang et al. | |
| 6,132,373 A * | 10/2000 | Ito et al. | 600/437 |
| 6,656,121 B2 | 12/2003 | Jeong et al. | |
| 6,835,177 B2 * | 12/2004 | Fritz et al. | 600/443 |
| 7,090,640 B2 * | 8/2006 | Barth et al. | 600/443 |
| 7,204,807 B2 * | 4/2007 | Tsoref | 600/438 |
| 7,727,153 B2 * | 6/2010 | Fritz et al. | 600/449 |
| 7,856,130 B2 * | 12/2010 | Suri et al. | 382/128 |
| 8,131,032 B2 * | 3/2012 | Demi et al. | 382/128 |
| 8,135,179 B2 * | 3/2012 | Wilson et al. | 382/110 |
| 8,450,703 B2 | 5/2013 | De Boer et al. | |
| 8,465,426 B2 * | 6/2013 | Kanai et al. | 600/437 |
| 8,771,191 B2 * | 7/2014 | Fritz et al. | 600/449 |
| 8,995,739 B2 * | 3/2015 | Xiao et al. | 382/131 |
| 9,014,452 B2 * | 4/2015 | Xiao et al. | 382/131 |
| 2004/0116808 A1 * | 6/2004 | Fritz et al. | 600/437 |
| 2004/0193048 A1 * | 9/2004 | Tsoref | 600/437 |
| 2005/0096528 A1 * | 5/2005 | Fritz et al. | 600/407 |
| 2005/0119555 A1 * | 6/2005 | Fritz et al. | 600/410 |
| 2007/0038092 A1 | 2/2007 | Jean-Claude et al. | |
| 2008/0205719 A1 | 8/2008 | Pekar et al. | |
| 2009/0274340 A1 * | 11/2009 | Wilson et al. | 382/110 |
| 2010/0036246 A1 | 2/2010 | Kushculey et al. | |
| 2010/0125202 A1 * | 5/2010 | Lee et al. | 600/443 |

FOREIGN PATENT DOCUMENTS

| | | |
|---|---|---|
| EP | 2189117 A1 | 5/2010 |
| JP | H05176925 A | 7/1993 |
| JP | 2000350727 | 12/2000 |
| JP | 2003038487 A | 2/2003 |

OTHER PUBLICATIONS

Isard et al: "Condensation-Conditional Density Propagation for Visual Tracking"; International Journal of Computer Vision, vol. 29 (1), 1998, pp. 5-28.

Jackson et al: "Generalized Equations for Predicting Body Density of Men"; British Journal of Nutrition (1978), vol. 40, pp. 497-504.

* cited by examiner

DEVICE FOR DETERMINING
TISSUE LAYER
BOUNDARIES OF A BODY

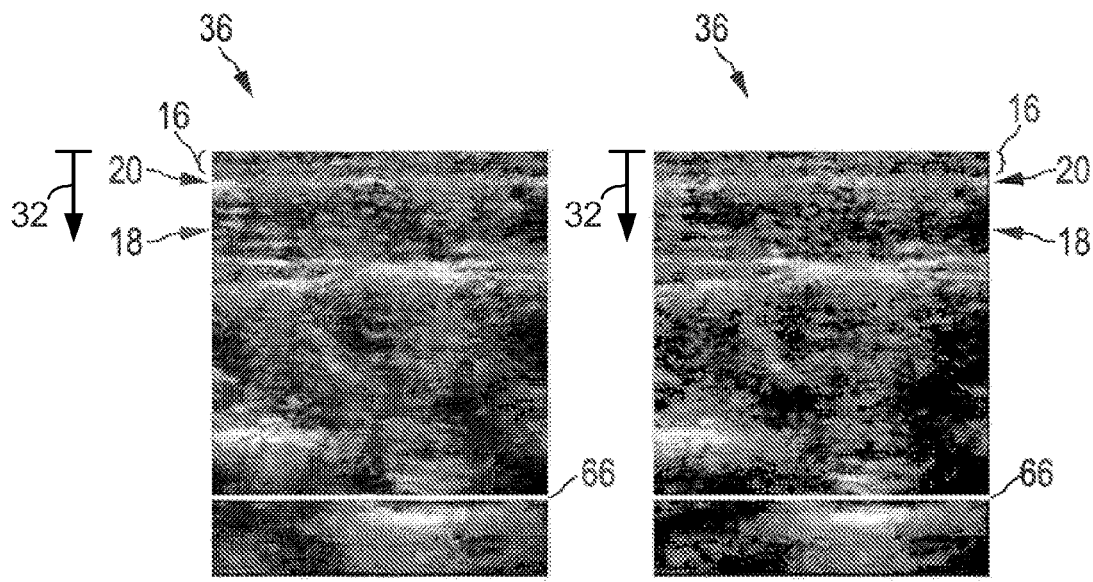
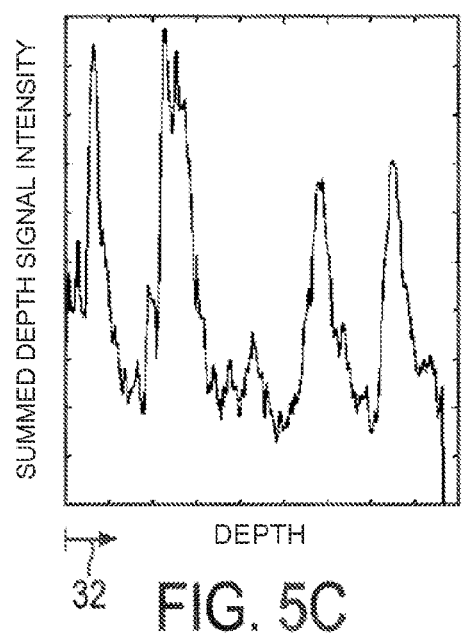
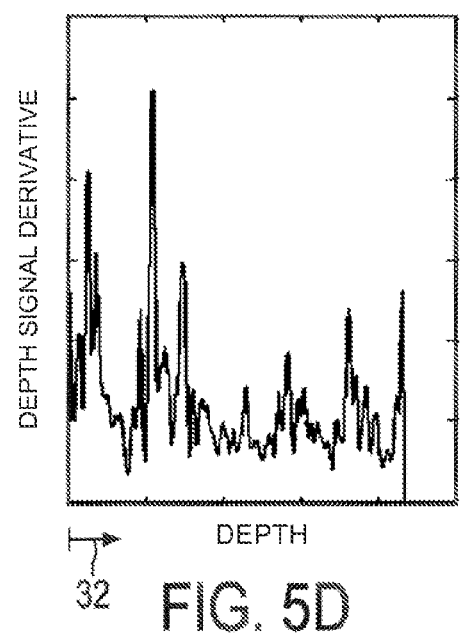
FIG. 5C      FIG. 5D

DEVICE AND METHOD FOR DETERMINING ACTUAL TISSUE LAYER BOUNDARIES OF A BODY

FIELD OF THE INVENTION

The present invention relates to a device and method for determining actual tissue layer boundaries of a body. The invention also relates to a device and method for estimating total values for fat and/or fat-free mass of a body. Further, the invention relates to a computer program for implementing said methods and to a processor for use in said devices.

BACKGROUND OF THE INVENTION

In the field of personal fitness appliances and personal health care it is desirable to get insight into a body's proportional composition of different tissue types. For this purpose it is necessary to distinguish several main tissues from each other. The most important tissues to detect from a health perspective are: fat mass and fat-free mass, lean body mass and muscle mass and a further discrimination of adipose tissue in subcutaneous and intra-abdominal adipose tissue. Commonly used solutions to detect tissue layers in body tissues use either modalities that are too complex to be used in a home setting like MRI scan, under-water weighting and skin fold measurements that require proper training to be meaningful or modalities that are too inconsistent to provide meaningful data such as bioelectrical impedance, which is very sensitive to the varying amount of water in the body. Furthermore these techniques are only capable of determining total mass of the selected tissue and do not provide insight into "on the spot" thicknesses of certain tissues. Other techniques involve either measurement with multi-beam and multi-focus ultrasound devices, but this involves heavy processing and costly hardware or makes prior assumptions about where the tissue layer should be. Due to the huge variation in body composition across the population such techniques cannot be applied widely.

Measuring body fat using ultrasound devices is disclosed for example in U.S. Pat. No. 5,941,825. This method measures body fat by transmitting into a body ultrasound pulses, measuring at least one reflective distance, selecting the at least one reflective distance, which has the shortest distance to indicate the distance between the inner and outer border of subcutaneous fat tissue, wherein the selecting of the at least one reflective distance corrects for an ultrasound transmission parallax. It is asserted that this allows for a more convenient and precise measurement of layer thicknesses in an object.

SUMMARY OF THE INVENTION

It is an object of the present invention to provide a method and device for more precise measurement of tissue layer boundaries of a body.

It is a further object to provide a device and method for estimating the total fat mass and/or fat-free mass of a body.

It is another object to provide a fat measurement device which can easily and conveniently be operated in a home setting.

In a first aspect of the present invention a device is presented for determining actual tissue layer boundaries of a body, comprising a probe for acquiring two or more ultrasound images at adjacent positions of a surface of the body, a converter for converting said ultrasound images separately to depth signals, wherein a depth signal is obtained by summing intensities of one of said ultrasound images along a line of substantially constant depth in the body, a detector for detecting a set of candidate tissue layer boundaries for an ultrasound image by thresholding the depth signal obtained for said ultrasound image, a selection means for selecting from a set of candidate tissue layer boundaries a nearest candidate tissue layer boundary that is nearest to the surface of the body, and a processing means for determining an actual tissue layer boundary from the nearest candidate tissue layer boundaries obtained for various ultrasound images.

In a further aspect of the present invention a device is presented for estimating total fat- and/or fat-free mass of a body, comprising a device for determining actual tissue layer boundaries of a body as proposed by the present invention and a body fat estimator for estimating the total fat- and/or fat-free mass of a body based on several actual tissue layer boundaries determined at different places of the body.

According to further aspects of the present invention corresponding methods, a computer program for implementing said methods, and a processor for use in said device are provided.

Preferred embodiments of the invention are defined in the dependent claims. It shall be understood that the claimed methods and computer program have similar and/or identical preferred embodiments as the claimed device and as defined in the dependent claims.

Different to the currently known devices of this art, the device according to the present invention acquires two or more ultrasound images at adjacent positions of the surface of the body and uses these images to determine a tissue layer boundary that appears spatially coherent on the acquired images.

The number of images acquired per position depends on how fast the user moves the probe. For example, if moving slowly, multiple images might be acquired at one position. This can be detected by the movement detection means (e.g., used in computer mice) included in the device. Typically, the area is large enough to cover the body (part) that needs to be measured.

The user moves the device along a surface of the person and thus obtains ultrasound images from a larger area compared to acquiring only one ultrasound signal or image from one fixed position. This allows for a more reliable detection of tissue layer boundaries. The inventors realized that, if the user measures only at one fixed position, there could be a small local anomaly in the fat layer at that position and the device might falsely interpret this as a tissue boundary, thus yielding a false estimate of the fat layer. On the other hand, with a device according to the present invention, the device is moved along an area on the surface of the body and several images are acquired. The local anomaly could be identified as an outlier and an accurate estimate be obtained. Because the several images are typically acquired at different time points, the images can also be referred to as frames of a video. Accordingly, it is also possible to use video processing methods for a more accurate identification of the tissue boundaries.

In a preferred embodiment of the present invention the selection means is adapted to select the nearest candidate tissue layer boundary only from among those candidate tissue layer boundaries that have a tissue boundary width exceeding a minimum tissue boundary width. According to this embodiment, it is assumed that the actual tissue layer boundary which is to be determined has at least a certain minimum tissue boundary width. The tissue boundary width of candidate tissue layer boundaries could be determined for example by counting the number of pixels for which the depth signal is higher than the threshold.

By using this condition it is ensured that noise or small anomalies in the images are not falsely detected as tissue layer boundary. The minimum tissue boundary width can be a preset constant or it could be dependent on parameters such as e.g. the patient's age or weight. The minimum tissue boundary width could also be chosen depending on the resolution of the acquired ultrasound images.

In a preferred embodiment of the invention, said nearest candidate tissue layer boundaries are depth values and said means for determining an actual tissue layer boundary is based on averaging said nearest candidate tissue layer boundaries obtained for various ultrasound images.

In another preferred embodiment of the present invention said processing means for determining an actual tissue layer boundary determines the actual tissue layer boundary based on the relative frequency of different nearest candidate tissue layer boundaries obtained for various ultrasound images, particularly by using the nearest candidate tissue layer boundary that occurs most frequently. Because ultrasound images are acquired at different adjacent positions, in general the depth values determined for these positions will be different. Using the average of these different depth values is the simplest way of determining one estimate of the actual tissue layer boundary. This approach is appropriate if the different depth values indeed correspond to the same tissue layer boundary. If, however, for some images false depth values are determined, for example because some of the images were corrupted by noise, it is appropriate to determine the actual tissue layer boundary based on the relative frequency of different depth values. For example, if for 20 ultrasound images a depth value of around 3 cm is determined, but for only three images a depth value of 10 cm is determined, it is more sensible to reject the 10 cm depth values and determine the actual tissue layer boundary as 3 cm.

In a preferred embodiment of the invention the detector detects a set of candidate tissue layer boundaries for an ultrasound image by thresholding a weighted sum of said depth signal and a derivative of said depth signal. The weighting can also be such that the thresholding is performed only on the derivative signal.

For example in the case of high background image intensity the derivative of the depth signal may be more informative than the depth signal itself.

In a preferred embodiment of the present invention, the probe is adapted for acquiring two or more ultrasound images at subsequent time points, wherein the device further comprises a visual tracking means for tracking tissue layer boundaries over images acquired at subsequent time points, wherein said visual tracking means is adapted to estimate a refined actual tissue layer boundary.

By making use of the temporal coherence (or continuity) between frames, tissue layer boundaries at each frame can be more accurately and reliably detected. For instance, looking at each individual frame, maybe there are too many uncertainties and it is ambiguous to decide where the tissue layer boundaries are. By tracking tissue layers across multiple frames, it becomes less uncertain or ambiguous to determine the tissue layers. In one embodiment, visual tracking algorithms can be used to track the deformation of the tissue layers in ultrasound videos. Multiple observations at frame 1 . . . t-1 can be used to estimate/track the tissue layer at frame t. For example, with particle filtering, the tissue layer detection can be formulated as $$p(x_t|z_{1:t}) = \kappa p(z_t|x_t) p(x_t|z_{1:t-1}),$$

$$p(x_t|z_{1:t-1}) = \int p(x_t|x_{t-1}) p(x_{t-1}|z_{1:t-1}) dx_{t-1}$$

where $x_t$ is the state of the tissue layer at frame t, and $z_{1:t}$ are the observations at frames 1 till t. This is described in more detail in Michael Isard and Andrew Blake, "CONDENSATION—Conditional Density Propagation for Visual Tracking", International Journal of Computer Vision, 29, 1, 5-28, (1998). A quantitative measurement, for example, the percentage or amount of fat or muscle mass, can be calculated from the ultrasound video.

According to a further aspect of the present invention a device is presented that estimates a total fat- and/or fat-free mass of a body. A total body fat value can be estimated based on the several actual tissue layer boundaries that were determined at different places of the body as previously described.

In a preferred embodiment of the present invention the total body fat value is estimated using a formula that involves a weighted sum of predetermined constants, an age of the person, a sum of actual tissue layer boundaries, a square of the sum of actual tissue layer boundaries, and/or a logarithm of the sum of actual tissue layer boundaries. Depending on the number of sites measured the following formulas for estimating body density (BD) can, for instance, be applied:

i) Method of Jackson & Pollock: "Generalized equations for predicting body density of men", British Journal of Nutrition (1978), 40: 497-504 Cambridge University Press:

For men:

7 site=>BD=1.11200000−0.00043499*(X1)+0.00000055*(X1)$^2$−0.00028826*(age)
BD=1.21394−0.03101*(log X1)−0.00029*(age)
3 site=>BD=1.1093800−0.0008267*(X2)+0.0000016*(X2)$^2$−0.0002574*(age)
BD=1.18860−0.03049*(log X2)−0.00027*(age)
BD=1.1125025−0.0013125*(X3)+0.0000055*(X3)$^2$−0.0002440*(age) with:

X1=Sum of chest, axilla, triceps, subscapula, abdomen, suprailium, thigh (in mm)
X2=Sum of chest, abdomen, thigh (in mm)
X3=Sum of chest, triceps and subscapula (in mm)
Age in years.

For women:

7 site=>BD=1.0970−0.00046971*(X1)+0.00000056*(X1)$^2$−0.00012828*(age)
BD=1.23173−0.03841*(log X1)−0.00015*(age)
4 site=>BD=1.0960950−0.0006952*(X2)+0.0000011*(X2)$^2$−0.00012828*(age)
BD=1.21993−0.03936*(log X2)−0.00011*(age)
3 site=>BD=1.0994921−0.0009929*(X3)+0.0000023*(X3)$^2$−0.0001392*(age)
BD=1.21389−0.04057*(log X3)−0.00016*(age)
BD=1.089733−0.0009245*(X4)+0.0000025*(X4)$^2$−0.0000979*(age) with:

X1=Sum of chest, axilla, triceps, subscapula, abdomen, suprailium, thigh (in mm)
X2=Sum of triceps, abdomen, suprailium, thigh (in mm)
X3=Sum of triceps, thigh, suprailium (in mm)
X4=Sum of triceps, suprailium, abdomen (in mm)
Age in years.

ii) Method of A. W. Sloan:
BD=1.1070−0.003845*(thigh)−0.001493*(iliac crest).

iii) The method of Siri et al. can be used for translating body density into body fat:

% Body Fat=(495/Body Density)−450.

The fat-free mass (FFM) can be calculated as weight minus fat-mass (FM) (i.e., FFM=Weight−FM).

In a further embodiment the device comprises a user interface for providing a user with instructions to place the probe at certain locations on the body. This embodiment makes the device easier to operate and makes sure that the measurements that were determined at different places of the body are used correctly in above-mentioned formulas.

In a further embodiment, the device further comprises a means for detecting movement of the probe, in particular movement of the probe that is tangential to the surface of said body, for determining the relative positions of the acquired ultrasound images. Knowing the relative positions of the acquired ultrasound images enables the device to know the size of the area where the ultrasound images were acquired. This information could be used in a refined version of above-mentioned formulas. Alternatively, the device could detect false placement or false movement of the probe and notify the user.

In a further embodiment, the device further comprises a means for comparing properties of said detected movement with properties of an expected movement. For example the device could notify the user if the probe is being moved too fast.

BRIEF DESCRIPTION OF THE DRAWINGS

These and other aspects of the invention will be apparent from and elucidated with reference to the embodiment(s) described hereinafter. In the following drawings FIG. 5A to FIG. 5G illustrate the processing steps for obtaining a nearest candidate tissue layer boundary from an ultrasound image.

DETAILED DESCRIPTION OF THE INVENTION

Figure 1:
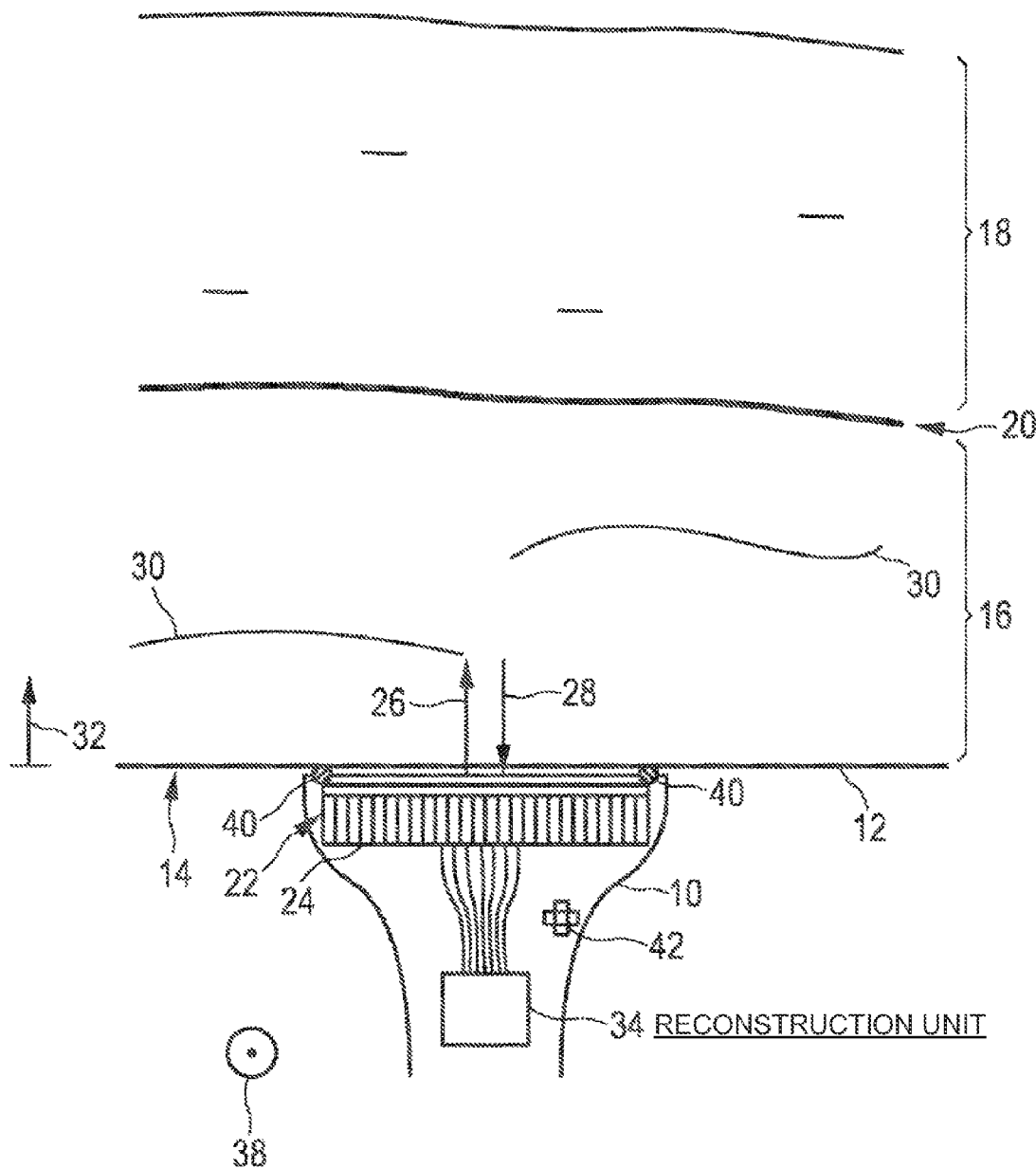
FIG. 1 shows how the probe is positioned on the surface of a body, which has two tissue layers.

FIG. 1 shows an example of a probe 10 that is placed on the surface 12 of the person's body 14. The body has a first and a second tissue layer 16, 18, which are separated by a tissue layer boundary 20. The first tissue layer 16 is fat, the second tissue layer 18 is some other tissue, for example muscle. The ultrasound probe 10 has a transducer 22, which comprises a number of elements 24 for transmitting ultrasound 26 and receiving reflected ultrasound 28. Ultrasound can mainly get reflected either from tissue layer boundaries 20 or from local tissue inhomogeneities 30. Usually, only a small percentage of the transmitted ultrasound 26 is reflected, so that ultrasound gets reflected also from tissue layer boundaries 20 or tissue inhomogeneities 30 that are located deeper inside the body. The arrow 32 indicates the direction of increasing depth. The elements 24 of the transducer 22 are connected to a reconstruction unit 34, which computes a two-dimensional image.

FIG. 1 shows that the reconstruction unit 34 is located on the probe 10; however, in general it can be located outside the probe 10. Although not explicitly shown, it is understood that the reconstruction unit 34 may also comprise a noise removal means, for example a noise removal means that is adapted to perform filtering or Otsu thresholding.

The user can move the probe 10 along a direction 38 that is tangential to the surface 12 of the body 14 and orthogonal to the plane of FIG. 1. For example, the user can slowly move the probe 10 along the user's belly in order to get a full measurement of the fat layer of the belly. The probe 10 comprises a tangential movement detection means 40, which can detect such tangential movement. The detection means 40 can be designed similar to the detection means that are used in computer mice, for example using an LED or laser with a corresponding photo detector. To determine the orientation of the ultrasound probe the probe further comprises an orientation sensor 42. While the user moves the ultrasound probe along the surface 12 of the body 14, the probe continuously acquires images 36. The images 36 thus correspond to adjacent positions on the surface 12 of the body 14. The images are typically 2D, but could also be 3D image volumes. The plurality of images 36 is sometimes also referred to as frames of an ultrasound video.

Figure 2:
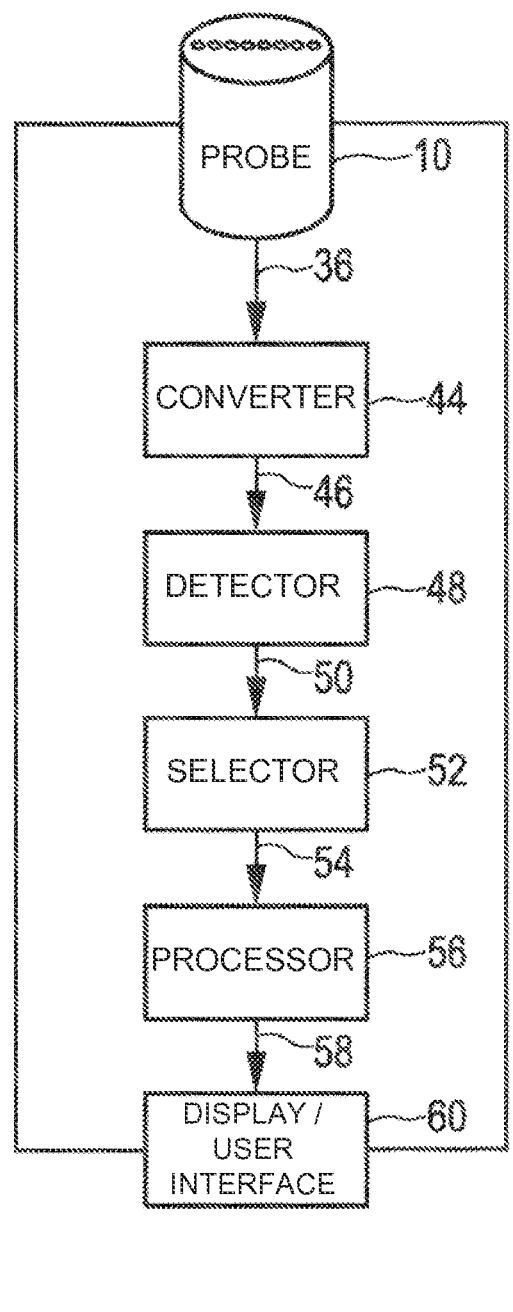
FIG. 2 is a schematic block diagram of a device for estimating an actual tissue layer boundary according to the present invention.
Figure 3:
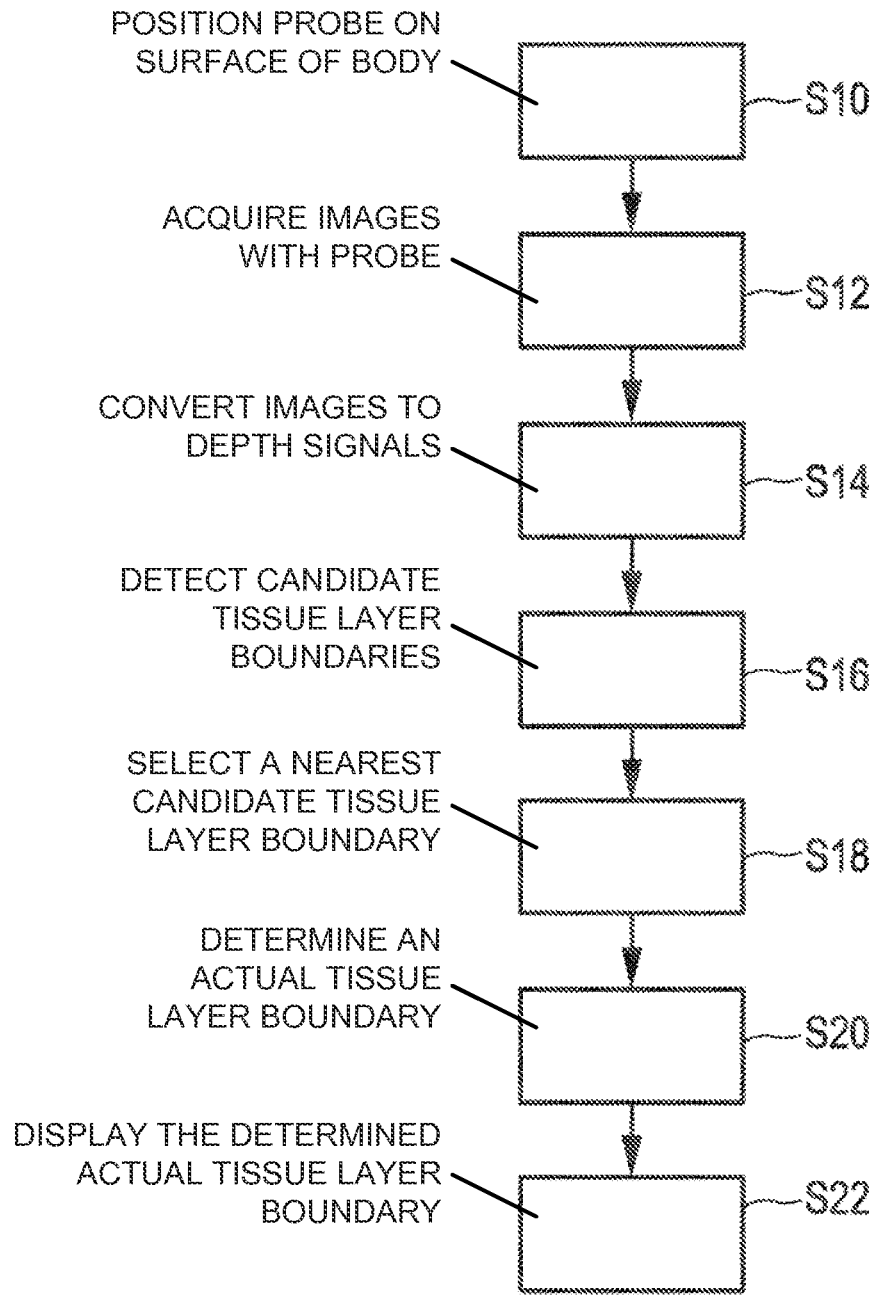
FIG. 3 is a flowchart of the method according to the present invention.

FIG. 2 shows a schematic block diagram of a device 8 according to the present invention, FIG. 3 shows a flowchart of the corresponding method.

In a first step S10, the probe 10 is positioned on the surface 12 of the body 14.

At step S12, images 36 are acquired with the probe 10.

At step S14, the converter 44 converts some of these images to depth signals 46 by summing the intensities of the image 36 along a line that corresponds to essentially constant depths in the body.

At step S16, the detector 48 uses thresholding of the depth signal 46 to detect candidate tissue layer boundaries 50.

At step 20, the selection means 52 selects from a set of such candidate tissue layer boundaries 50 a nearest candidate tissue layer boundary 54 that is nearest to the surface 12 of the body 14.

At step S20, the processing means 56 determines an actual tissue layer boundary 58 from said nearest candidate tissue layer boundaries, which were selected for various images 36.

At step S22, the actual tissue layer boundary 58 is displayed on a display 60. In addition to the display 60, the device 8 may also comprise a user interface, e.g. for changing settings of the tissue layer measurement.

Figure 4:
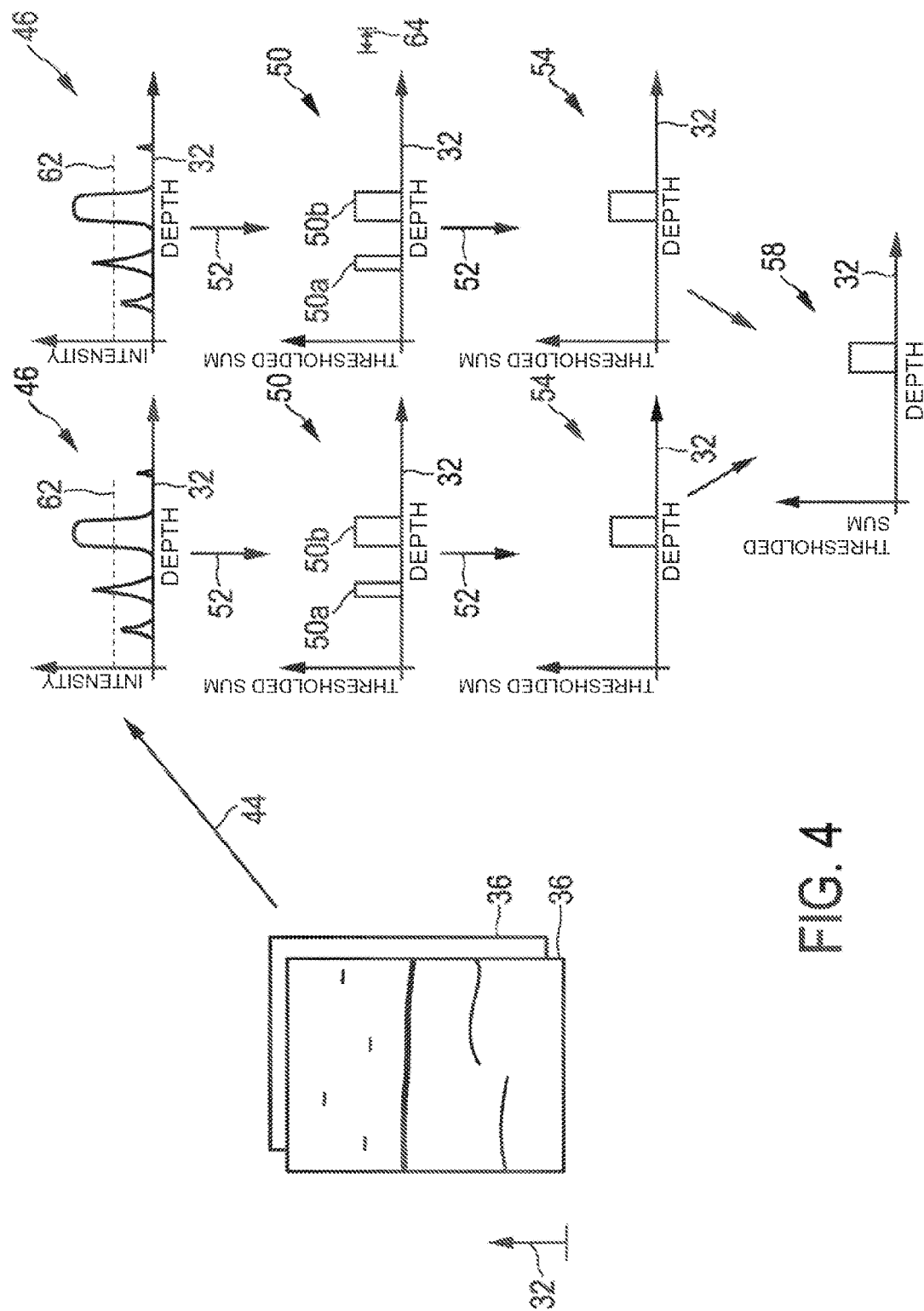
FIG. 4 shows a schematic view of two ultrasound images, the corresponding depth signals, the candidate tissue layer boundaries, nearest tissue layer boundaries, and the actual tissue layer boundary.

FIG. 4 shows a schematic view of how an actual tissue layer boundary 58 is determined from 2D ultrasound images 36. The images 36 are summed along lines that correspond to equal depths in the body 14. This conversion step 44 yields two depth signals 46. The depth signals 46 are shown in the figure as plots, where the horizontal axis corresponds to increasing depths within the body 14. The vertical axis corresponds to a higher value of the summed intensities. The threshold 62 is indicated with a dashed line. If the value of the depth signal 46 is higher than the threshold 62, a candidate tissue layer boundary 50 is detected at this position. The value of the threshold 62 can either be a fixed preset value or it can be dependent on the overall average intensity in the images 36. For example the threshold 62 could be designed as ten times the average intensity of one line corresponding to constant depth within the body.

For both of the images 36 two candidate tissue layer boundaries 50a, 50b are identified. The first candidate tissue layer boundary 50a is nearer to the surface of the body, however, it has a smaller width than the second candidate tissue layer boundary 50b. Because it is smaller than the required minimum width 64 it is rejected and the nearest candidate tissue layer boundary 54 is only chosen from among the remaining candidate tissue layer boundaries 50, in this case the second candidate tissue layer boundary 50b.

The processing means 56 determines the actual tissue layer boundary 58 by choosing the nearest candidate tissue layer boundary value 54 that occurs most frequently. If several depth values 54 occur with the same frequency, the average of those values is chosen as actual tissue layer boundary value 58.

FIG. 5A shows an acquired ultrasound image 36. The direction of increasing depth 32 is from top to bottom of the image, i.e., the top of the image corresponds to the surface 12 of the body 14. The image has rectangular dimensions, but in principle also other image dimensions would be possible. The image shows a fat layer 16, which is separated by a tissue layer boundary 20 from a second tissue layer 18.

FIG. 5B shows the same ultrasound image 36 after a noise removal process which is performed using Otsu thresholding. Also shown in FIGS. 5A and 5B is an example of a line 66 that corresponds to constant depth in the body 14.

FIG. 5C shows the depth signal 46 that is obtained by summing the noise-removed image 36 across horizontal lines 66. The direction of increasing depth 32 is now plotted horizontally from left to right.

FIG. 5D shows a derivative of the depth signal of FIG. 5C. The derivative in this case is computed as the absolute value of the mathematical derivative, i.e., it contains only positive values.

Figure 5E:
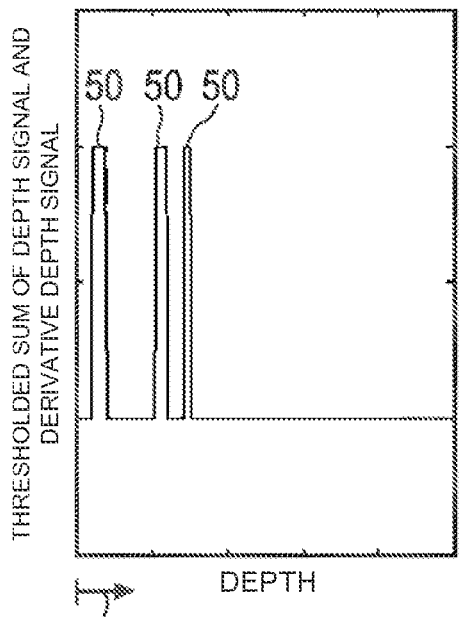

FIG. 5E shows the candidate tissue layer boundaries that are detected by thresholding a sum of the depth signal and the derivative depth signal. Subsequently, an outlier removal process takes place to remove candidates that spread only over a few lines (data points on the depth signal), for example by applying median filtering. At the interface between the probe 10 and the surface 12 of the body 14 ultrasound reflection 28 can occur. Although this is not visible in FIG. 5A, it is clear that in principle this can lead to high intensities in the upper part (corresponding to an area near the surface of the body) of an image 36. It is understood that precautions are taken that these are not falsely identified as nearest candidate tissue layer boundary 54. For example the first two lines of the images 36 could be excluded from the nearest candidate tissue layer boundary detection. This is an engineering trick to avoid false detections due to the ultrasound reflection between the probe 10 and the surface 12 of the body 14. Generally this can be done by examining the first several lines of the images 36 to see if there is ultrasound refection between the probe 10 and the surface 12 of the body 14.

Figure 5F:
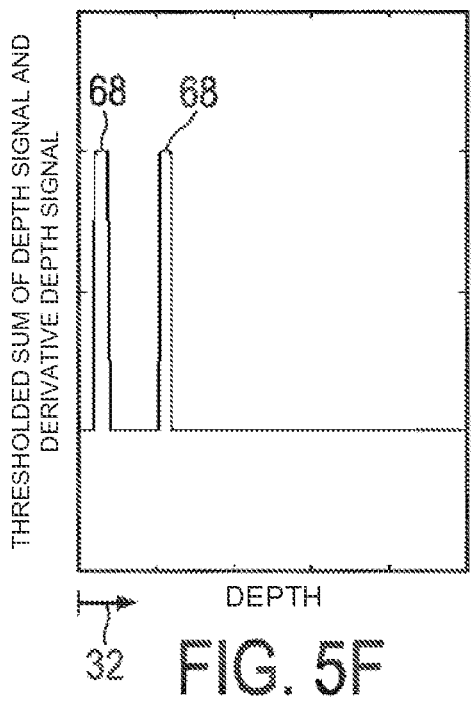

FIG. 5F shows the resulting candidate tissue layer boundaries 68 that have a tissue boundary width exceeding the minimum tissue boundary width 64.

Figure 5G:
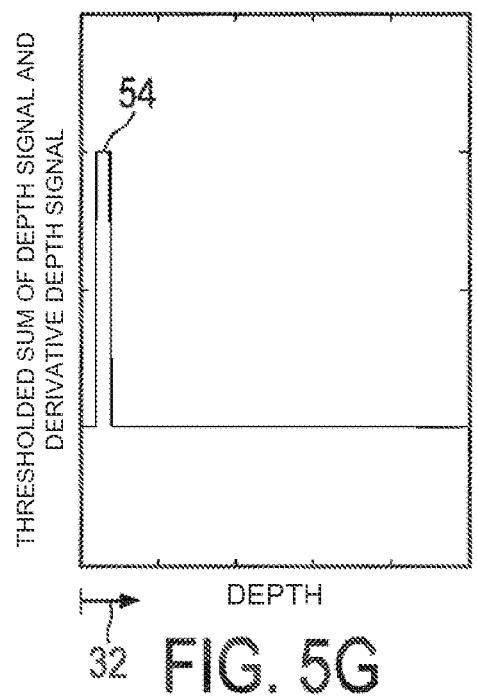

FIG. 5G shows the nearest candidate tissue layer boundary 54 that was selected by the selection means.

The detection of nearest candidate tissue layer boundaries is performed in a similar way for ultrasound images 36 acquired from adjacent positions. This way, for every acquired ultrasound image 36 a nearest candidate tissue layer boundary can be determined. Alternatively, the above-mentioned conversion, detection, and selection can be applied only to a subset of the acquired images, for example only for images that were acquired from positions on the surface with at least a certain minimum distance between them.

Figure 6:
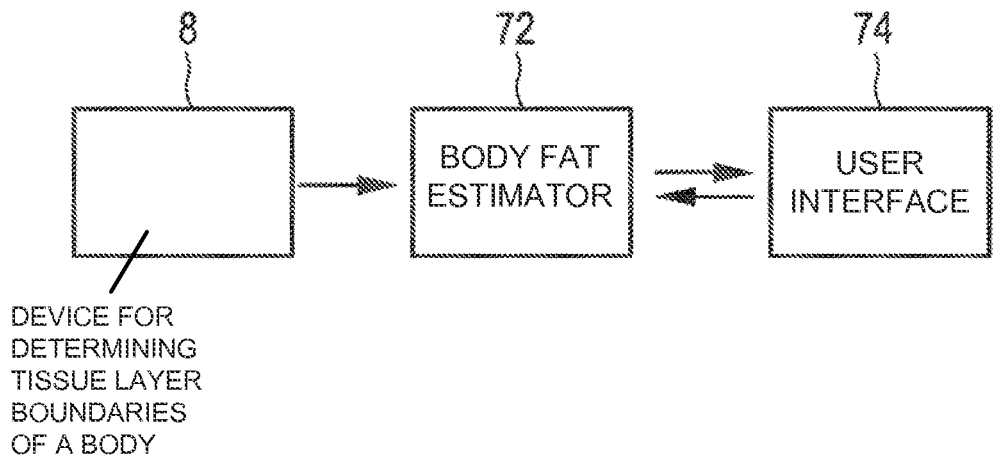
FIG. 6 is a schematic block diagram of a device for estimating a total body fat value according to the present invention.

FIG. 6 shows an example of an embodiment of a device 70 for estimating a fat- and/or fat-free mass of a body. The body fat estimator 72 uses actual tissue layer boundary values 58 that are determined by the device 8 for determining actual tissue layer boundaries. The determined actual tissue layer boundaries 58 can be shown on the user interface 74. The user interface 74 also provides further information about the measurement process and gives the user instructions on how to use the device 70, for example where to place the probe and how to move it. The user interface can comprise a (touch) screen, LEDs, dedicated buttons, and/or a loudspeaker. The user can also provide the device 70 with information through the user interface 74. For example, the user could enter additional data like e.g. the age and gender of the patient amongst others. Further, the user can indicate whether he wants to perform a measurement e.g. at 3, 5 or 7 sites. Based on this selection, the body fat estimator 72 would use the appropriate formula. Finally, the user interface 74 shows the estimated fat- and/or fat-free mass or the estimated body density.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for determining actual tissue layer boundaries of a body, from two or more ultrasound images acquired via a probe at adjacent positions of a surface of the body, the device comprising:
   a converter that separately converts said ultrasound images to depth signals, wherein a depth signal is obtained by summing intensities of a respective one of said ultrasound images along lines of substantially constant depth in the body;
   a detector that separately detects a set of candidate tissue layer boundaries for a respective ultrasound image by thresholding the depth signal obtained for said respective ultrasound image;
   a selector that separately selects from a set of candidate tissue layer boundaries for each respective ultrasound image a nearest candidate tissue layer boundary that is nearest to the surface of the body for the respective ultrasound image, wherein the selector further selects the nearest candidate tissue layer boundary only from among those candidate tissue layer boundaries that have a tissue boundary width exceeding a minimum tissue boundary width; and a processor that determines an actual tissue layer boundary from the nearest candidate tissue layer boundaries selected for each respective ultrasound image of the two or more ultrasound images.

2. The device according to claim 1, wherein said nearest candidate tissue layer boundaries comprise depth values and wherein said processor further determines the actual tissue layer boundary based on averaging said nearest candidate tissue layer boundaries selected for various ones of the two or more ultrasound images.

3. The device according to claim 1, wherein said nearest candidate tissue layer boundaries comprise depth values and wherein said processor further determines the actual tissue layer boundary based on a relative frequency of different nearest candidate tissue layer boundaries selected for various ones of the two or more ultrasound images, further wherein the determined actual tissue layer boundary comprises the nearest candidate tissue layer boundary that occurs most frequently.

4. The device according to claim 1, wherein said detector further separately detects a set of candidate tissue layer boundaries for a respective ultrasound image by thresholding a weighted sum of said depth signal and a derivative of said depth signal obtained for said respective ultrasound image.

5. The device according to claim 1, further comprising:
a probe for acquiring said two or more ultrasound images at subsequent time points; and
a visual tracking device adapted to track, via a visual tracking algorithm, tissue layer boundaries across multiple ultrasound images acquired at subsequent time points, wherein an output of said visual tracking device provides a temporal coherence between said two or more ultrasound images to enable tissue layer boundaries in each ultrasound image to be detected, via the detector, with an increased accuracy, enabling the processor to determine a refined actual tissue layer boundary.

6. The device for determining actual tissue layer boundaries of a body according to claim 1, further comprising:
a probe for acquiring the two or more ultrasound images at adjacent positions of a surface of the body.

7. A device for estimating a fat-mass and/or fat-free mass of a body, comprising:
the device for determining actual tissue layer boundaries of a body according to claim 1; and
a body fat estimator device that estimates total fat-mass and/or fat-free mass values of the body in response to several actual tissue layer boundaries determined at different places of the body.

8. The device according to claim 7, wherein the body fat estimator device further estimates the total body fat-mass and/or fat-free mass values in response to one of more of a weighted sum of predetermined constants, an age of the body, a sum of actual tissue layer boundaries, a square of the sum of actual tissue layer boundaries, and/or a logarithm of the sum of actual tissue layer boundaries.

9. The device according to claim 7, further comprising:
a user interface that provides a user with instructions for placing the probe at certain locations on the body.

10. The device according to claim 7, further comprising:
a movement detector that detects movement of the probe, wherein the movement of the probe includes movement that is tangential to the surface of the body, wherein an output of the movement detector provides information for determining, via at least the processor, relative positions of the two or more ultrasound images acquired via the probe.

11. The device according to claim 10, further comprising a a comparator that compares properties of said detected movement in response to the determined relative positions of the two or more acquired ultrasound images with one or more properties of an expected movement.

12. A method for determining actual tissue layer boundaries of a body from two or more ultrasound images acquired via a probe at adjacent positions of a surface of the body, the method comprising the steps of:
converting said ultrasound images separately to depth signals, wherein a depth signal is obtained by summing intensities of a respective one of said ultrasound images along lines of substantially equal depth in the body;
detecting a set of candidate tissue layer boundaries separately for a respective ultrasound image by thresholding the depth signal obtained for said respective ultrasound image;
selecting from a set of candidate tissue layer boundaries, separately for each respective ultrasound image, a nearest candidate tissue layer boundary that is nearest to the surface of the body, wherein selecting further comprises selecting the nearest candidate tissue layer boundary only from among those candidate tissue layer boundaries that have a tissue boundary width exceeding a minimum tissue boundary width; and
determining an actual tissue layer boundary from the nearest candidate tissue layer boundaries selected for each respective ultrasound image of the two or more ultrasound images.

13. A method for estimating fat-mass and/or fat-free mass values of a body, comprising the steps of:
determining actual tissue layer boundaries according to the method of claim 12 at several positions of the body; and
estimating, via a body fat estimator, a total body fat-mass and/or fat-free mass value of the body in response to several actual tissue layer boundaries determined at the several positions of the body.

14. A non-transitory computer-readable medium embodied with a computer program that comprises program code executable on a computer for causing the computer to carry out the steps of the method as claimed in claim 12.

* * * * *